(12) United States Patent
Greener

(10) Patent No.: US 11,964,093 B2
(45) Date of Patent: Apr. 23, 2024

(54) NEGATIVE PRESSURE DEVICE

(71) Applicant: Smith & Nephew PLC, Watford (GB)

(72) Inventor: Bryan Greener, York (GB)

(73) Assignee: Smith & Nephew PLC, Watford (GB)

(*) Notice: Subject to any disclaimer, the term of this patent is extended or adjusted under 35 U.S.C. 154(b) by 1102 days.

(21) Appl. No.: 16/503,279

(22) Filed: Jul. 3, 2019

(65) Prior Publication Data

US 2019/0321524 A1 Oct. 24, 2019

Related U.S. Application Data

(63) Continuation of application No. 14/881,022, filed on Oct. 12, 2015, now Pat. No. 10,716,881, which is a continuation of application No. 13/144,264, filed as application No. PCT/GB2010/050020 on Jan. 8, 2010, now Pat. No. 9,180,231.

(30) Foreign Application Priority Data

Jan. 12, 2009 (GB) .................................. 0900423

(51) Int. Cl.
*A61M 1/00* (2006.01)

(52) U.S. Cl.
CPC .............. *A61M 1/74* (2021.05); *A61M 1/682* (2021.05); *A61M 1/743* (2021.05); *A61M 1/96* (2021.05)

(58) Field of Classification Search
CPC ........ A61M 1/74; A61M 1/682; A61M 1/743; A61M 1/96; A61M 1/0035; A61M 1/0011; A61M 1/0088; A61M 1/0031; A61M 1/0066; A61M 1/0052; A61M 1/0072; A61M 1/0023
See application file for complete search history.

(56) References Cited

U.S. PATENT DOCUMENTS

| 3,572,340 A | 3/1971 | Lloyd et al. |
| 3,721,239 A | 3/1973 | Myers |
| 3,863,664 A | 2/1975 | Holbrook et al. |

(Continued)

FOREIGN PATENT DOCUMENTS

| CN | 1571682 | 1/2005 |
| FR | 1 163 907 | 10/1958 |

(Continued)

OTHER PUBLICATIONS

International Preliminary Report on Patentability, re PCT Application No. PCT/GB2010/050020, dated Jul. 12, 2011.

(Continued)

*Primary Examiner* — Quang D Thanh
(74) *Attorney, Agent, or Firm* — Knobbe, Martens, Olson & Bear, LLP

(57) ABSTRACT

A method and apparatus for providing negative pressure at a wound site. The apparatus includes a negative pressure reservoir and a reservoir valve for selectively connecting the reservoir to a wound chamber at a wound site. In particular, but not exclusively, the present invention relates to an apparatus including a source of negative pressure which acts as a negative pressure reservoir to continually or repeatedly "top up" an applied negative pressure so that negative pressure applied at a wound site can be maintained within desired limits for a relatively long period of time.

11 Claims, 3 Drawing Sheets

(56) References Cited

U.S. PATENT DOCUMENTS

| | | |
|---|---|---|
| 3,983,872 A | 10/1976 | Nehring |
| 3,991,763 A | 11/1976 | Genese |
| 4,388,922 A | 6/1983 | Telang |
| 4,392,860 A | 7/1983 | Huck et al. |
| 4,525,166 A | 6/1985 | Leclerc |
| 4,735,606 A | 4/1988 | Davison |
| 4,969,880 A | 11/1990 | Zamierowski |
| 5,549,584 A | 8/1996 | Gross |
| 5,549,585 A | 8/1996 | Maher et al. |
| 5,738,656 A | 4/1998 | Wagner |
| 5,876,387 A | 3/1999 | Killian et al. |
| 6,371,947 B1 | 4/2002 | Gibertoni |
| 6,824,533 B2 | 11/2004 | Risk, Jr. et al. |
| 7,700,819 B2 | 4/2010 | Ambrosio et al. |
| 8,007,257 B2 | 8/2011 | Heaton et al. |
| 8,062,272 B2 | 11/2011 | Weston |
| 8,157,775 B2 | 4/2012 | Bobroff et al. |
| 8,162,909 B2 | 4/2012 | Blott et al. |
| 8,273,368 B2 | 9/2012 | Ambrosio et al. |
| 8,323,264 B2 | 12/2012 | Weston et al. |
| 8,366,690 B2 | 2/2013 | Locke et al. |
| 8,382,731 B2 | 2/2013 | Johannison |
| 8,398,614 B2 | 3/2013 | Blott et al. |
| 8,679,081 B2 | 3/2014 | Heagle et al. |
| 8,715,256 B2 | 5/2014 | Greener |
| 8,785,059 B2 | 7/2014 | Hartwell |
| 8,808,259 B2 | 8/2014 | Walton et al. |
| 8,843,327 B2 | 9/2014 | Vernon-Harcourt et al. |
| 9,180,231 B2 | 11/2015 | Greener |
| 9,205,183 B2 | 12/2015 | Hartwell et al. |
| 2004/0054338 A1 | 3/2004 | Bybordi et al. |
| 2007/0185463 A1 | 8/2007 | Mulligan |
| 2007/0225663 A1 | 9/2007 | Watt et al. |
| 2007/0265585 A1 | 11/2007 | Joshi et al. |
| 2008/0108977 A1 | 5/2008 | Heaton et al. |
| 2008/0200905 A1* | 8/2008 | Heaton .................. A61M 1/82 604/543 |
| 2009/0030383 A1 | 1/2009 | Larsen et al. |
| 2010/0042021 A1 | 2/2010 | Hu et al. |
| 2010/0125259 A1* | 5/2010 | Olson .................... A61M 1/84 604/319 |
| 2010/0268177 A1 | 10/2010 | Hall |
| 2010/0318043 A1* | 12/2010 | Malhi .................. A61M 1/984 604/313 |
| 2011/0105963 A1 | 5/2011 | Hu et al. |
| 2011/0125113 A1 | 5/2011 | Adahan |
| 2012/0078207 A1* | 3/2012 | Hu ........................ A61M 1/912 604/319 |
| 2012/0109085 A1 | 5/2012 | McNeil |
| 2013/0018338 A1 | 1/2013 | Weston et al. |
| 2013/0253453 A1 | 9/2013 | Olson |
| 2013/0296816 A1 | 11/2013 | Greener |
| 2016/0095966 A1 | 4/2016 | Greener |

FOREIGN PATENT DOCUMENTS

| | | |
|---|---|---|
| WO | WO 1996/011031 | 4/1996 |
| WO | WO 2003/018098 | 3/2003 |
| WO | WO 2009/002260 | 12/2008 |
| WO | WO 2009/071928 | 6/2009 |
| WO | WO 2009/102021 | 8/2009 |
| WO | WO 2009/103031 | 8/2009 |
| WO | WO 2009/126103 | 10/2009 |

OTHER PUBLICATIONS

International Search Report, re PCT Application No. PCT/GB2010/050020, dated Apr. 29, 2010.
"Negative Pressure Wound Therapy", BlueSky Medical, Product Catalog 2006 (LBL-00224-01-AD), in 8 pages.
Notice of Opposition—Statement of Facts and Evidence, re European Patent No. EP 2 385 849, dated Jun. 5, 2019, in 11 pages.
Reply of the Patent Proprietor to the Notice(s) of Opposition, re the Opposition of European Patent No. EP 2 385 849, dated Oct. 25, 2019, in 25 pages.
Annex to the Communication—Provisional Non-Binding Opinion, the Opposition of European Patent No. 2385849, dated Jan. 23, 2020, 4 pages.
Brief Communication on Oral proceedings—Letter from the Opponent, re the Opposition of European Patent No. 2385849, dated Feb. 24, 2021, 4 pages.
Communication to the parties concerning termination of the opposition proceedings of the Patent for European Patent No. 10701711.3, dated Oct. 22, 2021, 2 pages.
Decision rejecting the opposition against the European Patent No. 2385849, dated Jul. 7, 2021, 19 pages.
Information about the Result of Oral Proceedings for the Opposition of European Patent No. 2385849, dated Apr. 21, 2021, 1 page.
New Summons to attend oral proceedings pursuant to rule 115(1) EPC for Patent No. 2385849, mailed on Oct. 14, 2020, 7 pages.
Reply from the Patent Proprietor to the Notice of Opposition of the European Patent No. 2385849, dated Jul. 17, 2020, 13 pages.
Written Submission by the Opponent for Opposition of European Patent No. EP2385849, dated Jul. 16, 2020, 3 pages.

* cited by examiner

NEGATIVE PRESSURE DEVICE

CROSS-REFERENCE TO RELATED APPLICATIONS

This application is a continuation of U.S. patent application Ser. No. 14/881,022, filed Oct. 12, 2015, which is a continuation of U.S. patent application Ser. No. 13/144,264, filed Jul. 12, 2011, now U.S. Pat. No. 9,180,231, which is a U.S. National Phase of PCT International Application No. PCT/GB2010/050020, filed on Jan. 8, 2010, designating the United States and published on Jul. 15, 2010 as WO 2010/079359, which claims priority to Great Britain Patent Application No. 0900423.5, filed on Jan. 12, 2009. The disclosure of each prior application is incorporated by reference herein in its entirety and should be considered part of this application.

BACKGROUND OF THE DISCLOSURE

Field of the Invention

The present invention relates to an apparatus and method for providing negative pressure at a wound site. In particular, but not exclusively, the present invention relates to an apparatus including a source of negative pressure which acts as a negative pressure reservoir to continually or repeatedly "top up" an applied negative pressure so that negative pressure applied at a wound site can be maintained within desired limits for a relatively long period of time.

Description of the Related Art

Devices for the generation of negative pressure at the surface of skin have been used for many hundreds of years to treat animal and human bodies. For example the cupping technique (which relates to the positioning of a mouth of a rigid vessel containing hot air) is a well known technique. Spring powered syringes and suction cups are other mechanical techniques which have been used in the past for generating a vacuum on tissue. In common with cupping such techniques have, in the past, suffered from a very limited longevity of the therapy which can be applied. That is to say the duration of the negative pressure which can be maintained over a site of application has been limited.

To enable a more prolonged application of controlled negative pressure, powered systems, which include a vacuum generation source such as a pump of some type have been developed and many examples of such systems are used today for the management of wounds. However, many of these systems are not convenient for discreet use by a patient as they are large, can be heavy and are often noisy. Furthermore the production costs associated with such systems are substantial due largely to the cost of materials and complexity of assembly.

Attempts have been made to produce a mechanical device able to apply negative pressure to a wound site. It will be appreciated that such a mechanical device, due to its simplicity of design, would be expected to reduce material costs and assembly costs. For example, U.S. 2008/200905 discloses a hand-pump system for the application of negative pressure at a tissue site. However, the system described does not enable prolonged convenient application of negative pressure at the wound site and in fact requires re-evacuation relatively often. This is a serious deficiency particularly as many such systems should ideally be useable overnight.

SUMMARY OF SOME EXEMPLIFYING EMBODIMENTS

It is an aim of the present invention to at least partly mitigate the above-mentioned problems.

It is an aim of certain embodiments of the present invention to provide an apparatus which can be manufactured and assembled in a convenient and thus cost effective manner yet which can provide a negative pressure at a wound site within desired pressure limits over a period of time prolonged with respect to prior art techniques.

It is an aim of certain embodiments of the present invention to provide one, two or more negative pressure reservoirs or a series of negative pressure reservoirs which act as backups for the negative pressure generated at a wound site.

It is an aim of certain embodiments of the present invention to provide a system for applying negative pressure at a wound site which can remain active for at least ten hours without user interference being needed to cause re-evacuation. This enables a user to sleep undisturbed.

According to a first aspect of the present invention there is provided apparatus for providing negative pressure at a wound site, comprising:
 a negative pressure reservoir; and
 a reservoir valve for selectively connecting the reservoir to a wound chamber at a wound site.

According to a second aspect of the present invention there is provided a method of providing negative pressure at a wound site, comprising the steps of:
 via a reservoir valve, selectively connecting a negative pressure reservoir to a wound chamber at a wound site.

Certain embodiments of the present invention enable the prolonged application of reduced pressure at a wound site in a convenient and cost effective manner. For example a reduced pressure device can create a safe reduced pressure at the site of application (i.e. no greater than 200 mmHg below ambient atmospheric pressure) that is connected by at least one valve to at least one further negative pressure reservoir. By selectively connecting a high vacuum (i.e. greater than 200 mmHg below ambient atmospheric pressure) stored in the reservoir to the wound site via a pressure regulating valve the duration of therapy can be prolonged and also a desired negative pressure level at the wound site can be set and maintained.

Certain embodiments of the present invention utilise multiple negative pressure reservoirs each of which is independently connected via a control valve and conduit to a contact chamber formed at a wound site. This has the advantage that the user is able to select the appropriate pressure for the wound. Multiple valves set at different pressures e.g. 50 mmHg, 75 mmHg and 100 mmHg can be attached to a single reservoir to allow the user to select a pressure by isolation or lock down of the 2 valves not in use with simple shut off valves. Also malfunction of an individual control valve does not disable the whole system.

Certain embodiments of the present invention utilise a series of negative pressure reservoirs cascading one into another and eventually a contact chamber and separated by respective control valves. This has the advantage that a safety mechanism is built into the device such that a single failure (e.g debris in the valve) of a valve does not result in the wound being exposed to excessive possibly dangerous pressures. Aptly the largest reservoir is the one set at the most negative pressure in order to get maximum longevity of therapy for size of product. Also the mechanical properties of each reservoir can be tailored to provide optimal vacuum performance over a specified negative pressure range.

BRIEF DESCRIPTION OF THE DRAWINGS

Embodiments of the present invention will now be described hereinafter, by way of example only, with reference to the accompanying drawings in which.

In the drawings like reference numerals refer to like parts.

DETAILED DESCRIPTION OF SOME EXEMPLIFYING EMBODIMENTS

Figure 1A:
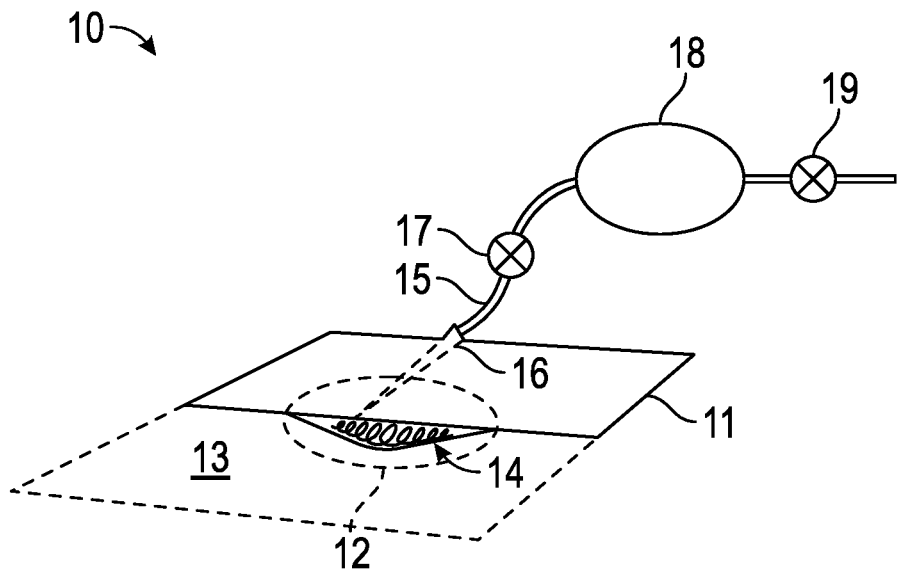
FIGS. 1A and 1B illustrate a wound site.
Figure 1B:
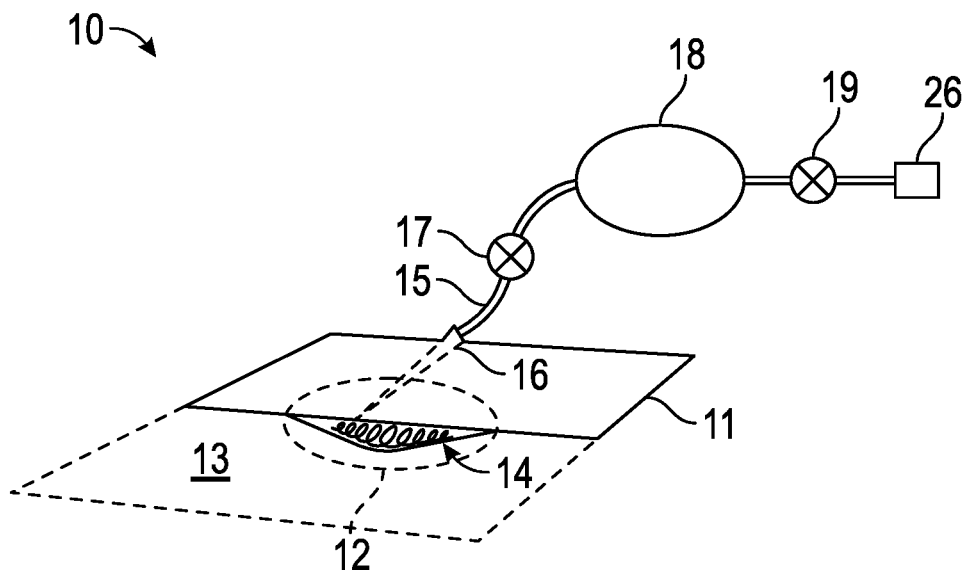

FIGS. 1A and 1B illustrate a location 10 where topical negative wound therapy (NPWT) is to be applied at a wound site. FIGS. 1A and 1B illustrate a cutaway (approximately half shown) view of a drape 11 which, in use, is located over and around a wound site 12. The drape 11 acts as a dressing covering the wound and may be any type of dressing normally employed with NPWT and, in very general terms, may comprise, for example a semi-permeable flexible, self-adhesive drape material as is known in the dressings art to cover the wound and seal with surrounding sound tissue 13 to create a sealed cavity or void over the wound. This sealed cavity or void is referred to hereinafter as a wound chamber 14. Hereinafter a chamber is taken to mean an enclosed volume of any geometry. The chamber may be of fixed or flexible geometry.

As illustrated in FIGS. 1A and 1B which also illustrate a cross section through the wound site 10 wound packer material may be used in the cavity between a wound bed and the drape to enable an even vacuum distribution to be achieved over the area of the wound. The packer material can be any suitable material as will be understood by those skilled in the art for example, a porous foam or gauze material that remains porous to fluid under the levels of vacuum created and which permits transfer of fluid across the entirety of the wound area. It is to be noted that the invention is not restricted to the particular geometry of the lumen entry design shown.

An aspiration conduit 15 is located through a pinched section 16 of the drape 11 so as to provide a sealed tubular conduit under the drape into the wound site. The wound packer and aspiration conduit thus cooperate to resist crushing under the levels of vacuum created at the wound site and permit transfer of wound exudates across the wound area to the aspiration conduit sealed to the flexible cover drape which extends over the wound.

The aspiration conduit may be a plain flexible tube, for example, having a single lumen therethrough and made from a plastics material compatible with raw tissue. However, the aspiration conduit may alternatively have a plurality of lumens therethrough to achieve specific objectives. A portion of the tube sited within the wound chamber may aptly have a structure to enable continued aspiration and evacuation of wound exudate without becoming constricted or blocked even at the high levels of negative pressure envisaged.

It is envisaged that the negative pressure range for the apparatus embodying the present invention may be between about −50 mmHg and −200 mmHg (note that these pressures are relative to normal ambient atmospheric pressure thus, −200 mmHg would be around 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg. Aptly the pressure of the wound chamber is between −125 mmHg and −20 mmHg. It will thus be appreciated that negative pressure is taken to mean a pressure that is less than ambient atmospheric pressure.

The aspiration conduit 15 thus has an end proximate to the dressing and wound site. At a distal end remote from the dressing and wound site the aspiration conduit is secured to a valve 17. This in turn is connected via a conduit to a negative pressure reservoir 18 and further control valve 19. A fluid communication path is thus established between the valve 19, negative pressure reservoir 18, reservoir valve 17 and wound chamber 14.

Whilst embodiments of the present invention will be described hereinafter by way of reference to a wound chamber 14 defined at a wound site under a drape it will be understood that certain embodiments of the present invention can be utilised to maintain a negative pressure in a wound chamber which is a rigid structure or partly rigid structure such as a cup device placed over a wound site.

Figure 2A:
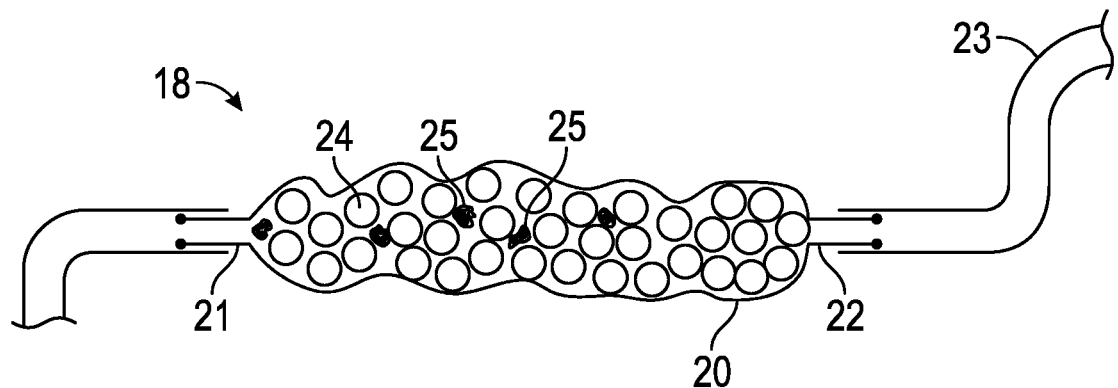
FIGS. 2A and 2B illustrate a collapsible negative pressure reservoir.
Figure 2B:
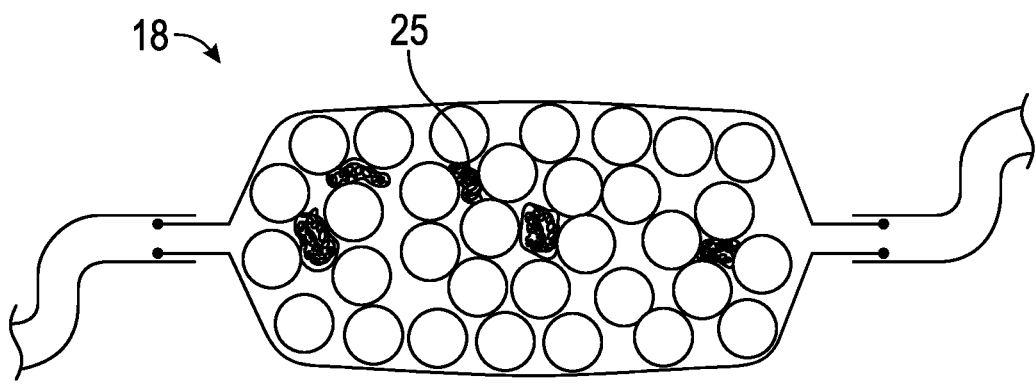

FIGS. 2a and 2b illustrate a negative pressure reservoir 18 in more detail according to a particular embodiment of the present invention. As illustrated in FIG. 2a the reservoir 18 is formed from a flexible body 20 having a wound site side orifice 21 connected to a tube connected to the reservoir valve in a sealed manner and a pump side orifice 22 connected to a conduit 23 connected to the control valve 19. Filler material 24 is located within the flexible body 20. The filler material 24, illustrated as many collapsible and expandable beads prevents total collapse into a zero volume for the negative pressure reservoir 18 when the reservoir is pumped so as to produce a negative pressure.

It will be understood that rather than containing many resilient beads one or more blocks of resilient material such as foam could be utilised within the reservoir body 20 to prevent collapse. It is advantageous that as a negative pressure established in the negative pressure reservoir 18 diminishes the filler expands so as to increase the volume in the reservoir. Aptly the filler material is selected so that expansion occurs over the whole range of pressures experienced in the negative pressure reservoir. This can be achieved by using a single resilient material having a characteristic which makes the filler expand over a broad pressure range or by providing filler materials of different materials. For example some of the beads 24 may be manufactured of a material which expands over a particular pressure range whilst other beads are manufactured of a different material which expands over a different pressure range.

Absorber material is aptly held in the negative pressure reservoir. The absorber material can be any type of material able to absorb wound exudate or other liquid being drawn from the wound site into the reservoir 18 through the aspiration tube 15 and reservoir valve 17. The absorber 25 is aptly an absorber gel such as ISOLYSEL™. The absorbent can be separated from the filler material (as shown) or be integral therewith. An added advantage of using such a gel matrix is that when exudate is stored excessive movement of the liquid is prevented such as slopping of the liquid. This also minimises bacterial growth and minimises odours.

FIG. 2b illustrates the negative pressure reservoir 18 in an expanded mode in which the negative pressure stored has become less negative. This occurs for example as a negative pressure at a wound site drops due to leakage around the periphery of the drape 11 or pinched region 16. When this occurs a pressure differential across the reservoir valve 17 causes the valve to open. The negative pressure in the reservoir thus acts to "top up" the negative pressure in the wound site chamber. Wound exudate may of course be drawn into the reservoir. As the negativity of the negative pressure established in the negative pressure reservoir 18 reduces the resilience of the filler material 24 is such that the expandable body 20 expands outwardly. This is illustrated by the diameter of the beads 24 shown in FIG. 2a expanding in FIG. 2b as well as the general expansion of the bag like body. FIG. 2b also illustrates how the absorbent material 25 absorbs liquid so as to expand also within the reservoir 18.

It will be appreciated that the various tubes are connected to the fluid reservoir via a fluid tight connection which might be either a tight friction fit or a fitting which requires some securing mechanism such as a jubilee clip or the like. Further examples of possible methods of connection may be adhesive, welding or use of a snap together connector for example as manufactured by Colder Products.

Returning to FIGS. 1A and 1B in use a drape is located over a wound site which may optionally include wound packer material. When the drape 11 is duly located a wound chamber is duly formed. The aspiration tube 15 provides a fluid communication path into this wound chamber 14. The reservoir valve 17 and control valve 19 are opened and a pump 26 (shown in FIG. 1B) is used to provide a desired negative pressure at the wound site. Subsequent to the desired pressure being attained the reservoir valve 17 is closed. This can be an automatic process or can be carried out manually. The pump 26 continues to evacuate the reservoir 18 to a desired, far more negative, pressure. This causes the flexible body 20 in the form of a bag and filler to collapse into the state shown in FIG. 2a. Subsequent to a desired high negative pressure being established in the negative pressure reservoir the control valve 19 is closed. This can be an automatic process or can be manually achieved. Thereafter the pump 26 is removed from the system.

Over time it is inherent that small leakage paths are formed between the drape 11 and surrounding tissue 13. Also it is possible that leakage paths are created around the pinched region 16 in the drape. As a result the negative pressure applied at the wound site degrades, that is to say becomes less negative over time. The negative pressure reservoir valve 17 is selected to open and close automatically responsive to a pressure difference between the pressure in the aspiration tube 15 and wound site and the tubing and negative pressure reservoir 18. As the negative pressure in the wound site increases the reservoir valve 17 opens providing a fluid communication path between the wound chamber and the negative pressure reservoir. The result is that the wound chamber pressure becomes more negative whilst the negativity of the negative pressure in the reservoir 18 reduces. Over time the valve 17 opens and closes continually or repeatedly so as to deplete the source of negative pressure in the reservoir. During this period of time the negative pressure applied at the wound site is maintained as much as possible within desired negative pressure ranges.

As a result the prolonged application of a reduced pressure is enabled at the tissue site in a convenient and cost effective manner. A safe reduced pressure of, for example, no greater than 200 mmHg below ambient atmospheric pressure is created and applied at the site of application. The valves connecting the reservoir to the wound site are fail safe and will only open when there is a loss of vacuum within the wound chamber. Furthermore the valves are selected so as to close when the pressure at the wound site reaches a desired target specified by the pressure valve manufacturer. Thus by connecting a high vacuum reservoir to a wound site via a pressure regulating valve the duration therapy can be prolonged in contrast to the prior art.

An example of a vacuum pressure regulation valve of a type suitable according to certain embodiments of the present invention is the VRD-ANB-CD vacuum regulator as supplied by Beswick Engineering™. It will be appreciated that other fluid flow control valves used to turn on and off a flow of fluid can be utilised according to certain embodiments of the present invention.

Figure 3:
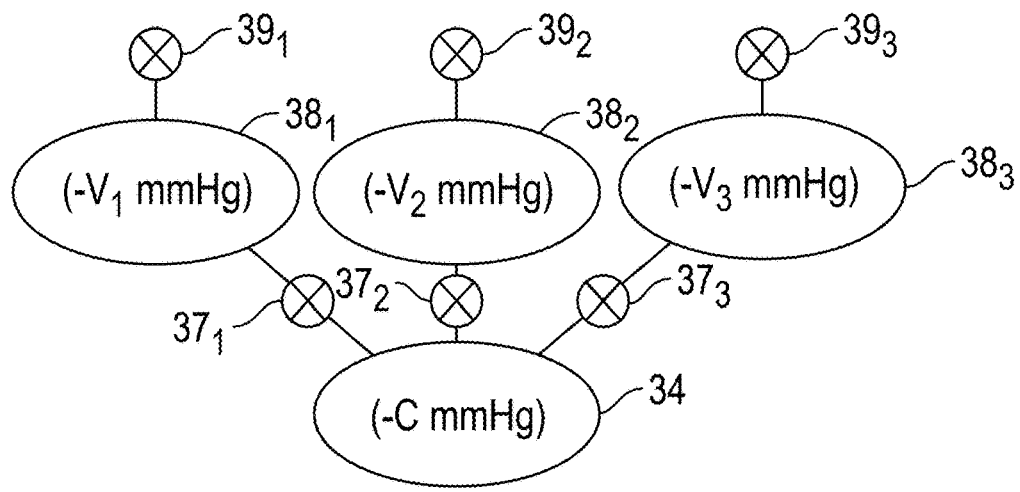
FIG. 3 illustrates a parallel arrangement of negative pressure reservoirs.

FIG. 3 illustrates an alternative embodiment of the present invention in which the wound chamber 34 at a wound site is in fluid communication with three separate negative pressure reservoirs $38_{1-3}$ via respective fluid communication paths through respective reservoir valves $37_{1-3}$. An advantage of connecting multiple negative pressure reservoirs independently to a wound chamber is that such parallel connections offer a degree of functional redundancy which can be important if one or more connecting valves becomes dysfunctional or parts of the wound chamber become physically separated (for example by local compression). An advantage also is that the provision of multiple negative pressure reservoirs means that the negative pressure originally set in each reservoir can be independently selected. For example as illustrated in FIG. 3 a negative pressure given the subscript 1 in the first negative pressure reservoir $38_1$ has a first value $-V_1$ whilst a negative pressure value in the second and third negative pressure reservoirs $38_2$, $38_3$ have respective values $-V_2$ and $-V_3$. By providing reservoir valves for each reservoir and ensuring that the valves are set to open and close at desired pressure differences the opening and closing of reservoirs can be selected so as to maximise the comfort to a user, period of time over which a desired negative pressure can be applied at a wound site. This also allows pressure to be applied in a more gradual rate to the user e.g. for painful wounds where the pressure may need to be slowly increase over a few hours or days.

Figure 4:
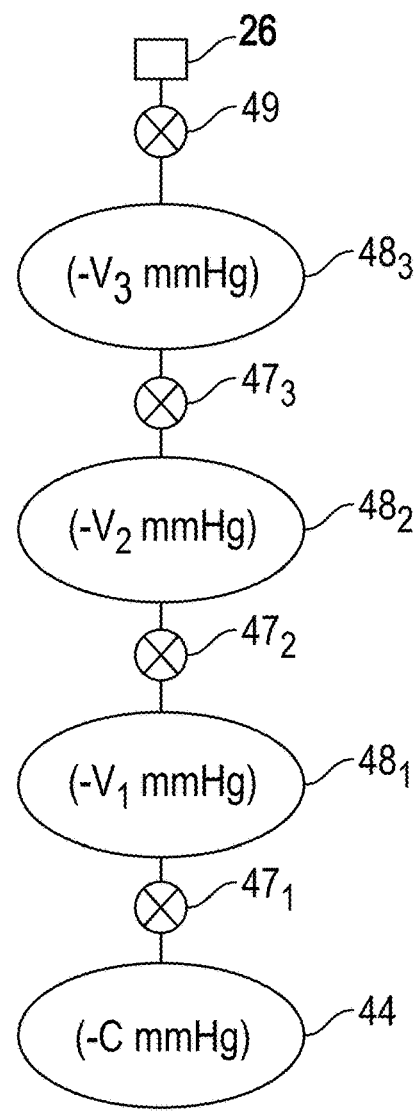
FIG. 4 illustrates separate negative pressure reservoirs connected in a series arrangement to a contact chamber formed at a wound site.

FIG. 4 illustrates an alternative embodiment of the present invention in which a wound chamber 44 is in a series connection with three negative pressure reservoirs $48_{1-3}$ by cascading a series of negative pressure reservoirs each separated from one another by respective reservoir valves $47_{1-3}$. The reservoir $48_1$ in direct communication with the wound chamber 44 may be at the same or greater negative pressure than the wound chamber. In turn a second negative pressure reservoir $48_2$ connected to the first negative pressure reservoir $48_1$ by reservoir valve $47_2$ may be at the same or greater negative pressure than the first negative pressure reservoir. The third negative pressure reservoir $48_3$ which is connected to the second negative pressure reservoir $48_2$ by a respective reservoir valve $47_3$ may be at the same or more negative pressure than the second negative pressure reservoir. A control valve 49, which is similar to the control valve 19, connected to the pump 26 are also illustrated.

Series connection of negative pressure reservoirs is useful for the controlled delivery of vacuum to the wound chamber. Pressure surges can be avoided in the event of single valve failure.

It will be appreciated that a combination of series and parallel connected negative pressure reservoirs can be utilised according to certain embodiments of the present invention. Also that one, two or more negative pressure reservoirs can be utilised.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A method of providing reduced pressure treatment to a tissue site, the method comprising:
    storing a negative pressure within a first reservoir with a pump;
    delivering a desired negative pressure from a second reservoir fluidically connected to the tissue site, wherein the first reservoir and the second reservoir are connected in series by a single conduit adapted to provide fluid communication between the first reservoir and the second reservoir; and
    responsive to a pressure difference between the second reservoir and the first reservoir, reducing pressure within the second reservoir by allowing fluid communication between the first reservoir and the second reservoir,
    wherein reduced pressure is communicated from the pump through a first valve to the first reservoir and subsequently through a second valve to the second reservoir, and
    wherein the pump, the first valve, the first reservoir, the second valve, and the second reservoir are arranged in series along the single conduit.

2. The method of claim 1 wherein storing the negative pressure comprises opening the first valve to allow flow of reduced pressure from the pump coupled to the first reservoir.

3. The method of claim 1 further comprising disallowing fluid communication between the first reservoir and the second reservoir in response to a second pressure difference between the second reservoir and the first reservoir.

4. A method of providing reduced pressure treatment to a tissue site, the method comprising:
    storing a negative pressure within a first chamber with an external reduced-pressure source;
    delivering a desired therapy pressure from a second chamber comprising an outlet port to the tissue site, wherein the first chamber and the second chamber are connected in series by a single conduit adapted to provide fluid communication between the first chamber and the second chamber; and
    responsive to a pressure difference between the second chamber and the first chamber, reducing pressure within the second chamber by allowing fluid communication between the first chamber and the outlet port of the second chamber,
    wherein reduced pressure is communicated from the external reduced-pressure source through a first valve to the first chamber and subsequently through a second valve to the second chamber, and
    wherein the external reduced-pressure source, the first valve, the first chamber, the second valve, and the second chamber are arranged in series along the single conduit.

5. The method of claim 4 wherein storing the negative pressure comprises opening the first valve to allow flow of reduced pressure from the external reduced-pressure source coupled to the first chamber.

6. A reduced pressure treatment system comprising:
    a dressing adapted to be positioned at a tissue site;
    a first reservoir adapted to be in fluid communication with the dressing and adapted to deliver a desired negative pressure to the tissue site at a first negative pressure level;
    a second reservoir adapted to store a negative pressure at a second negative pressure level;
    a single conduit adapted to provide fluid communication between the first reservoir and the second reservoir, wherein the single conduit pneumatically connects the first reservoir and the second reservoir in series;
    a first valve positioned in the single conduit, the first valve adapted to close in response to a first pressure difference between the first reservoir and the second reservoir and open in response to a second pressure difference between the first reservoir and the second reservoir; and
    a second valve coupled to the second reservoir and adapted to be in fluid communication with a pump to permit evacuation of the second reservoir to an increased negative pressure,
    wherein negative pressure is communicated from the pump through the second valve to the second reservoir and from the second reservoir through the first valve to the first reservoir, and
    wherein the first valve, the first reservoir, the second valve, and the second reservoir are arranged in series along the single conduit.

7. The system of claim 6, wherein the desired negative pressure is between about −50 mm Hg and −200 mm Hg.

8. The system of claim 6, wherein the desired negative pressure is about −125 mm Hg.

9. A reduced pressure treatment system comprising:
    a dressing adapted to be positioned at a tissue site;
    a first chamber comprising an output port adapted to be in fluid communication with the dressing and adapted to deliver a desired therapy pressure to the tissue site at a first negative pressure level;
    a second chamber adapted to store a negative pressure at a second negative pressure level;
    a single conduit adapted to provide fluid communication between the first chamber and the second chamber, wherein the single conduit pneumatically connects the first chamber and the second chamber in series;
    a first valve operably associated with the single conduit, the first valve adapted to substantially close in response to a first pressure difference between the first chamber and the second chamber and to open in response to a second pressure difference between the first chamber and the second chamber; and a second valve coupled to the second chamber and adapted to be fluidly coupled to an external reduced-pressure source to permit reduction of pressure in the second chamber, wherein negative pressure is communicated through the second valve to the second chamber and from the second chamber through the first valve to the first chamber, wherein the first valve, the first chamber, the second valve, and the second chamber are arranged in series along the single conduit.

10. The system of claim 9, wherein the desired therapy pressure is in a range of about −50 mm Hg to about −200 mm Hg.

11. The system of claim 9, wherein the desired therapy pressure is over −100 mm Hg.

* * * * *